United States Patent [19]

Biola et al.

[11] 3,947,476

[45] Mar. 30, 1976

[54] PROCESS FOR THE CONTINUOUS PREPARATION OF PROPYLENE OXIDE

[75] Inventors: Georges Biola, Venissieux; Gérard Schneider, Caluire, both of France

[73] Assignee: Rhone-Progil, Decines, France

[22] Filed: Jan. 25, 1974

[21] Appl. No.: 436,673

[30] Foreign Application Priority Data

Jan. 26, 1973 France .............................. 73.02719

[52] U.S. Cl. ......................................... 260/348.5 V
[51] Int. Cl.² ...................................... C07D 301/06
[58] Field of Search ................... 260/348.5, 348.5 V

[56] References Cited
UNITED STATES PATENTS

| | | | |
|---|---|---|---|
| 2,741,623 | 4/1956 | Millidge et al. | 260/348.5 V |
| 3,222,382 | 12/1965 | Lanthier | 260/348.5 V |
| 3,238,229 | 3/1966 | Reid | 260/348.5 V |

FOREIGN PATENTS OR APPLICATIONS

| | | | |
|---|---|---|---|
| 786,301 | 11/1957 | United Kingdom | 260/348.5 V |
| 933,548 | 8/1963 | United Kingdom | 260/348.5 V |
| 654,279 | 12/1962 | Canada | 260/348.5 V |

*Primary Examiner*—Norma S. Milestone
*Attorney, Agent, or Firm*—Bacon & Thomas

[57] ABSTRACT

A liquid phase continuous process for producing propylene oxide comprising oxidizing propylene with a molecular oxygen-containing gas in a solvent which is (*a*) water-insoluble and (*b*) as immiscible with organic carboxylic acids as possible; condensing the gaseous reaction products; adding water to the condensed reaction products to dissolve any undissolved acids contained therein; separating the aqueous phase from the resulting two-phase (aqueous and organic) system; recycling the organic phase to the reaction; and removing from the reaction a liquid containing propylene oxide and recovering the propylene oxide therefrom.

8 Claims, 1 Drawing Figure

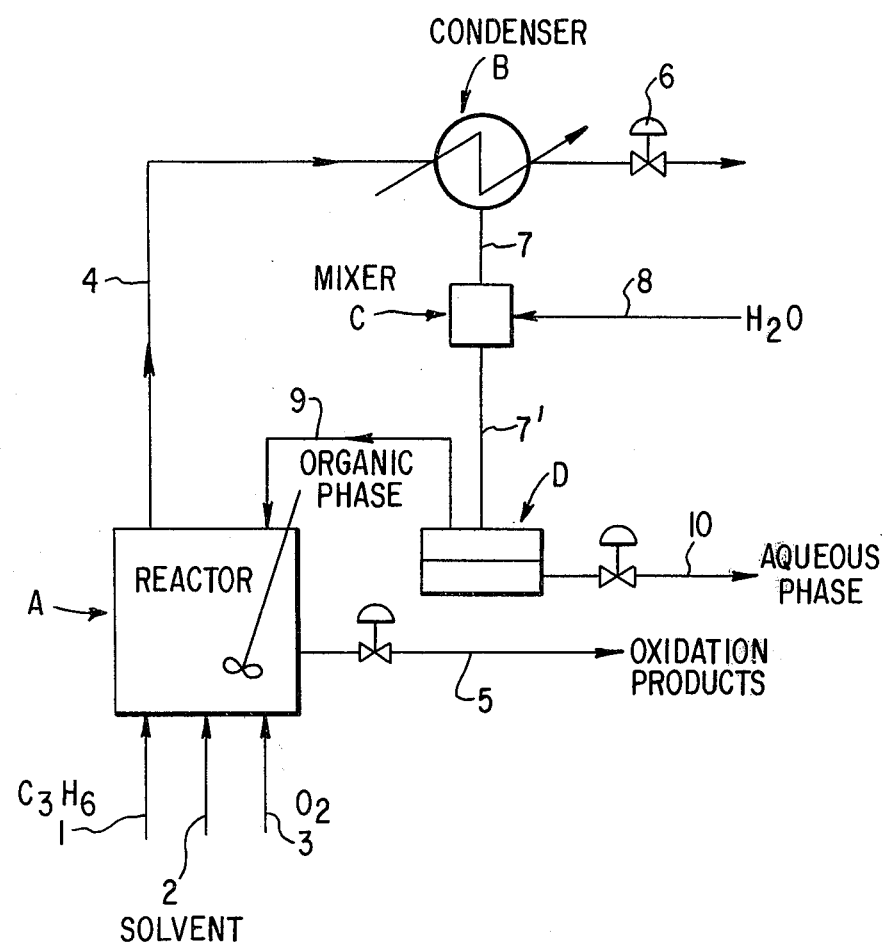

PROCESS FOR THE CONTINUOUS PREPARATION OF PROPYLENE OXIDE

BACKGROUND OF THE INVENTION

1. Field of the Invention

The present invention relates to a continuous process for the preparation of propylene oxide.

2. Description of the Prior Art

It is known that in processes for preparing propylene oxide by the oxidation of propylene with a molecular oxygen-containing gas in a liquid phase, a number of by-products are formed, some of which are particularly troublesome due to the reactions which they provoke or difficult separation they involve.

It is thus known that formic acid, and to a lesser extent acetic acid, formed during the reaction, react quickly with epoxides (H. W. Gibson — Chem. rev. 1960 — 5 — 675; W. J. HIckinbottom et al. *J. Chem. Soc.* — 1954 — 4200) and particularly with propylene oxide, especially in the presence of small quantities of water, to give not only propylene glycol and its esters, but also heavier products consisting mainly of polypropylene glycols more or less esterified by the acids.

On the other hand, alcohols are equally produced, during the oxidation reaction of propylene, which give esters by reaction with the acids. Among these esters, methyl formate is particularly troublesome for its boiling point is very near that of propylene oxide, which makes separation thereof difficult and expensive. The other esters, such as isopropyl or propylene glycol formate, can also create complications during separation operations due to their modiocre stability, especially in the presence of water.

It has been noted that the production of heavy products was all the more significant since the concentration in acids, particularly in formic acid, is higher in the reaction mixture. The same holds true for the esters.

Under normal conditions of propylene oxidation in liquid phase using molecular oxygen, acids and propylene oxide are found in the reaction mixture in variable quantities, but the ratio of concentrations thereof is practically constant when the reaction is carried out in a given solvent. This practically constant ratio is the consequence of the mechanism of formation of propylene oxide by the oxidation of propylene in liquid phase (A. V. Bobolev et coll. — Zh. Fiz. Khim — 1970 — 44 — 4 — 1028).

It has been proposed (French Pat. No. 1,414,707) in order to remove this formic acid, to carry out the oxidation of propylene in liquid phase in the presence of a solid neutralizing agent such as sodium carbonate suspended in the liquid. Such a process however, involves the formation of $CO_2$ and necessitates a filtration operation of the produced sodium formate which is insoluble in the reaction mixture, and therefore the process is rendered difficult.

It has also been proposed (U.S. Pat. No. 2,784,202) to treat the liquid phase leaving he vessel with a solution of sodium bicarbonate. However, such a process presents the drawback of making the process for recovery of the acid more complicated.

There is a need therefore, for a solution to the above problems and particularly, there is a need for a technique of removing or reducing the acid formed as a by-product in the reaction solution.

SUMMARY OF THE INVENTION

The primary object of the present invention is to provide a process for producing propylene oxide, by the oxidation of propylene, which is free of the above difficulties.

It is another object of this invention to provide a liquid phase process for producing propylene oxide by the direct oxidation of propylene wherein organic acids, particularly formic acid, are removed, at least partially, from the reaction mixture.

It is yet another object of this invention to provide such a process whereby said removal is accomplished simply.

It is a further object of the invention to provide a continuous liquid phase process for the direct oxidation of propylene to propylene oxide, as a result of the (at least) partial removal of organic acid impurities from the reaction mixture.

In general, a liquid phase propylene oxide process comprises contacting propylene with a gas containing molecular oxygen in a solvent and condensing the reaction product gases to produce a liquid reaction product containing (in addition to various propylene oxidation products) at least solvent, organic acids (and other impurities), unreacted propylene and water. The propylene oxide may then be separated and recovered.

The present invention provides a simple, yet effective, technique for at least partially removing the organic acid impurities. Essentially, the present invention resides in using, as the solvent, one which is water-insoluble and which is as immiscible as possible (preferably totally immiscible) with the organic acids (notably formic acid) and injecting water into the condensed reaction products thereby producing a two-phase system comprised of an aqueous phase (containing predominantly the organic acids dissolved therein) and an organic phase (containing predominantly unreacted propylene and solvent). The phases are then separated and the organic phase is recycled to the reaction from which a liquid is removed which contains propylene oxide and which is substantially free of said organic acids, esters thereof and related heavy products.

As a result of the addition of water, most or all of the organic acid impurities are removed prior to recycle to the reaction, and the entire process may be operated in a continuous fashion.

Other objects and advantages will become apparent from the ensuing description.

BRIEF DESCRIPTION OF THE DRAWINGS

The FIGURE is a flow sheet which schematically illustrates the process of the present invention.

DESCRIPTION OF THE PREFERRED EMBODIMENTS

Referring to the FIGURE, the process of the present invention is schematically illustrated by the flow sheet shown therein. To reactor A are fed propylene via stream 1, solvent via stream 2 and a molecular oxygen-containing gas (e.g., air) via stream 3. The reaction is conducted at an elevated temperature, and suitable means are provided to heat the reaction mixture in reactor A. The gas reaction products are drawn off via stream 4 and fed to condenser B where they are totally condensed. A valve 6 is normally provided which may be used to vent any uncondensed gases. The condensed reaction products are then fed, via stream 7, to a mixer C to which is also fed water via stream 8. Thereafter, the mixture is fed via stream 7' into decantation or separation device D wherein a two-phase system is produced, an upper organic phase and a lower aqueous phase. The organic phase, which consists predominantly of unreacted propylene and solvent is recycled to the reactor via stream 9 and the aqueous phase is discharged through stream 10, the aqueous phase containing most of the organic acid impurities contained in the reaction product stream together with other impurities such as esters, propylene derivatives, etc. The oxidation products, containing the desired propylene oxide, are drawn from the reactor via stream 5, from which the desired propylene oxide can be separated and recovered by any conventional technique.

Any gas containing molecular oxygen can be employed in the process of the present invention, as long as the gas does not contain any other material which would be reactive under the reaction conditions. Air is the preferred molecular oxygen-containing gas.

The reaction temperature is that temperature which is sufficient to conduct the liquid phase oxidation of propylene to produce propylene oxide, with the temperature usually being within the range 120°–250°C. The pressure in the reaction zone is normally within the range of 30–100 Bars (1 Bar equaling 0.9869 atmospheres of pressure).

The conditions of the condensation operation are not critical and may be varied to achieve the desired result, total condensation of the gaseous products. Generally however, the condensing operation is carried out within the range of from 15° to 20°C.

The amount of water added to the condensed reaction products is at least that amount of water necessary to totally dissolve the organic acid impurities present therein. This amount normally is equal to an amount of up to 5 kilograms of water per cubic meter (NTP) of molecular oxygen contained in the gas fed to the reaction zone. It is possible, if a sufficient amount of water is produced during the reaction, to eliminate this additional water fed to the mixing device. In other words, if a sufficient amount of water is produced during the reaction to dissolve substantially all of the organic acid impurities contained in the reaction products, no additional water need be added thereto. However, the separation of these organic acid impurities is favored by the presence of additional water, and it is therefore preferred to add an amount of water of up to 5 kilograms thereof per cubic meter of molecular oxygen fed to the reactor.

In the decantation device, the upper lighter organic phase is separated from the lower heavier aqueous phase. In the latter of course, the organic acid impurities are contained since they preferentially dissolve in the water phase. Therefore, the organic phase which is recycled to the reactor is substantially free of acidic impurities, notably formic acid, thereby decreasing the concentration of such impurities in the reaction zone.

The solvent which is used in the reaction is not particularly critical as long as it is insoluble in water and is as immiscible as possible with the organic acids formed during the reaction, notably formic acid. Desirably, the solvent is totally immiscible with such organic acid impurities. Any solvent having these characteristics can be employed in the process of the present invention, as long as it is otherwise inert under the reaction conditions. Preferred solvents include monochlorobenzene, the di(o,m, or p)-chlorobenzenes, the tetra(1,2,3,4-, 1,2,3,5- or 1,2,4,5-)-chlorobenzenes, and mixtures thereof. However, other solvents having the above solubility characteristics may be employed in the practice of this invention and it is not intended to limit the invention to only the preferred solvents.

The now presently preferred conditions of operation are as follows. Preferably, all operations should be conducted in apparatus composed or constructed of or lined with titanium in order to avoid impurities introduced into the products from the apparatus. The temperature and pressure preferably ranges from 140° to 200°C. and from 40 to 80 Bars, respectively. The solvent is selected from among the preferred solvents, the condensing operation is carried out at a temperature of from 15° to 20°C. and water is injected into the condensed products at a temperature lower than 25°C.

Further, the oxidation operation may be carried out in the presence of an optional catalyst, with any known catalyst useful for this purpose being operable in the present invention, such as molybdenum, tungsten or vanadium naphthenates or acetylacetonates, etc. Optionally, the catalyst may be omitted, and it is not intended to limit the operable catalysts to those exemplified above. It is the intention that any catalyst, having the capability of catalyzing the propylene to propylene oxide reaction, is useful in the present invention. Those skilled in the art are aware of such catalysts, and no attempt will be made here to provide additional examples, since the oxidation reaction of propylene to propylene oxide is known per se, and those skilled in the art are aware of catalysts useful in such a known process.

The process of the present invention has the advantage over prior art processes of permitting the easy separation of acidic impurities from the unreacted propylene which is recycled to the reaction zone, notably the separation of formic acid therefrom. In addition, this has the result of decreasing the concentration of such impurities in the reaction zone which alleviates the disadvantages discussed above. The separation is accomplished basically by the presence of water, preferably the addition of extraneous water to mixer C wherein the organic acid impurities are dissolved in the resulting aqueous phase in an uncombined form, these impurities preferentially being dissolved in the aqueous phase rather than in the organic phase since the solvent used in the process is insoluble in water and is only sparingly soluble or immiscible with the organic acid impurities.

The amount of molecular oxygen fed to the reactor is not critical as long as a sufficient amount of molecular oxygen is fed thereto to accomplish the oxidation reaction. The preferred amount of molecular oxygen is at least the stoichiometric amount required to convert propylene into propylene oxide. Those skilled in the art can vary this amount as desired.

In actuality, the condenser merely cools the reaction product gases down to a certain temperature, preferably 15°–20°C., resulting in a mixture of a gas and liquid phase in the condenser. The liquid phase is composed of unreacted propylene, any water formed during the reaction, oxidation products, etc., while the gas phase is generally composed of unreacted molecular oxygen, nitrogen gas assuming air is used as the molecular oxygen-containing gas, carbon monoxide, carbon dioxide, and possibly gaseous unreacted propylene. It is normally not efficient to attempt to totally condense the gas stream removed from the reactor, but this stream should be cooled down to such a temperature to condense substantially all of the oxidation products, solvent, water and as much of the unreacted propylene as is possible. The gases are vented from the condenser while the liquid phase is fed to the mixing device where additional water is added if necessary.

Thus, the process of the present invention provides an efficient process for the direct oxidation of propylene to propylene oxide using molecular oxygen wherein the concentration of organic acid impurities is substantially reduced in the reaction zone thereby avoiding the drawbacks of prior art processes noted above.

The present invention will be further illustrated by reference to the following examples which are intended to be illustrative and not limiting in effect.

EXAMPLE 1

The apparatus used was composed of titanium and includes the elements shown in the FIGURE. Into a 10 liter reactor was introduced, per hour:

16.536 kg of 1,2,4-trichlorobenzene (TCB);
3.708 kg of propylene; and
2.170 m³ of air The temperature was kept at 163°C. and the pressure at 60 Bars. The residence time of the reaction phase in the reactor was 0.38 hour. Gases escaping from the reactor were cooled down to 20°C. in condenser (B); i.e., a separation into an gas phase and a liquid phase is realized in condenser (B).

The gases vented from the condenser have a flowrate of 2.419 m³/hr. and have the composition shown in Table 1.

The liquid phase was fed to a decantation device having a volume of 0.3 liter, no additional water being added thereto.

The lower aqueous phase is drawn off continuously from the decantation apparatus (D) and its composition is given in Table 1.

The upper phase, rich in propylene, was recycled to the reactor.

So as to maintain the level of reaction mixture constant, 19.442 kg per hour of an organic phase, the composition of which is given in Table 1, was drawn off from the reactor (stream 10).

In Table 1, as in the following tables, the following are included in the "various products": methanol, isopropanol, allyl alcohol, acetaldehyde, propanol, acrolein and acetone; the formates other than methyl formate consist of isopropyl, allyl and propylene-glycol formates.

EXAMPLE 2

Example 1 was repeated under the conditions indicated in Tables 1 and 3; particularly the temperature was 183°C. instead of 163°C.

The results obtained are given in Table 1.

EXAMPLES 3 To 8

Example 1 was repeated at different temperatures with the introduction, at about 15°C., into the liquid phase coming out of the condenser of decreasing quantities of water with regard to the quantity of molecular oxygen introduced into the reactor.

The reaction conditions and results obtained are indicated in Tables 1 and 3.

EXAMPLE 9

The procedure of Example 1 was repeated with the reaction being conducted in the presence of 10 ppm, based on propylene, of molybdenum catalyst in the form of molybdenum naphthenate. The conditions of reaction and the results are shown in Table 1 and 3.

EXAMPLES 10 To 13

The procedure used in Examples 1 to 8 was repeated using monochlorobenzene instead of trichlorobenzene as a solvent.

The reaction conditions and results obtained are indicated in Tables 2 and 3.

EXAMPLES 14 AND 15

(for comparative purposes)

Example 1 was repeated using acetone as a solvent under the conditions indicated in Tables 2 and 3.

The results obtained are shown in Table 2.

Table 3 shows that:

1. If acetone is used as a solvent, formic acid cannot be removed from the reaction mixture, due to the total miscibility of acetone with water and formic acid (Examples 14 and 15); it is noticed that the concentration of formic acid in the reactor is high, that the formation of heavy products and formates is significant, and that the selectivity is poor.
2. If a solvent insoluble in water and sparingly miscible with formic acid, such as the mono- and trichlorobenzenes, is used, formic acid is partially removed due to the presence of water produced in the reaction (Example 1 and 2).
3. If, moreover, water is injected into the condensed products, the quantity of removed formic acid increases, and the quantities of produced formates and heavy products decrease (Examples 3-8, 11 and 13).
4. The process of the present invention produces equally good results when the process is conducted in the presence of a catalyst (Example 9).

If Examples 1 to 13 are performed according to the prior art, (i.e., without the optional injection of water and without separating the aqueous phase from the organic phase after condensation) the drawbacks observed in Examples 14 and 15 (i.e., a high concentration of formic acid in the reactor and a significant formation of heavy products and formates) would result.

TABLE 1

| Examples | 1 | 2 | 3 | 4 | 5 | 6 | 7 | 8 | 9 |
|---|---|---|---|---|---|---|---|---|---|
| Feed to reactor A | | | | | | | | | |
| solvent* | TCB | TCB | TCB | TCB | TCB | TCB | TCB | TCB | TCB |
| solvent rate (kg/hr) | 16.536 | 17.841 | 18.450 | 19.440 | 16.370 | 10.480 | 15.630 | 25.408 | 18.020 |
| $C_3H_6$ (kg/hr) | 3.708 | 4.304 | 3.570 | 3.185 | 3.707 | 3.168 | 3.482 | 4.325 | 3.846 |
| Air (m³/hr) | 2.170 | 2.940 | 0.943 | 0.840 | 1.236 | 1.372 | 1.198 | 1.809 | 1.088 |

Gases Leaving Condenser B
gas rate (m³/hr)
composition (% by vol.)

TABLE 1-continued

| Examples | 1 | 2 | 3 | 4 | 5 | 6 | 7 | 8 | 9 |
|---|---|---|---|---|---|---|---|---|---|
| $O_2$ etc | | | | | | | | | |
| gas rate (m³/hr) | 2.419 | 3.393 | 1.013 | 0.850 | 1.358 | 1.534 | 1.276 | 2.121 | 1.230 |
| $O_2$ | 1.6 | 1.1 | 1.1 | 0.8 | 0.9 | 1.1 | 0.9 | 0.9 | 1.3 |
| $N_2$ | 68.6 | 67.4 | 70.6 | 69.8 | 68.4 | 68.6 | 70.8 | 65.9 | 67.2 |
| $C_3H_6$ | 25.0 | 25.8 | 25.0 | 26.0 | 26.8 | 26.2 | 24.8 | 28.8 | 27.9 |
| CO | 1.2 | 2.0 | 0.9 | 0.9 | 1.1 | 1.0 | 1.0 | 1.4 | 1.1 |
| $CO_2$ | 3.6 | 3.7 | 2.4 | 2.5 | 2.8 | 3.2 | 2.5 | 3.0 | 2.5 |
| Aqueous Phase leaving Decantation Device D (kg/hr) | 0.126 | 0.231 | 1.016 | 0.865 | 0.525 | 0.550 | 0.402 | 0.769 | 0.554 |
| Composition (% wt.) | | | | | | | | | |
| $H_2O$ | 44.8 | 32.6 | 89.8 | 91.1 | 78.1 | 76.8 | 74.1 | 76.4 | 85.5 |
| PGL* | — | 17.9 | 1.0 | 1.3 | 4.9 | 5.0 | 5.2 | 6.7 | 5.8 |
| HCOOH | 32.2 | 20.1 | 4.3 | 3.9 | 9.8 | 10.7 | 10.3 | 9.6 | 4.5 |
| $CH_3COOH$ | 6.3 | 5.6 | 1.0 | 0.6 | 1.3 | 1.5 | 1.6 | 2.0 | 0.6 |
| HCOOMe (i.e., methyl formate) | 9.5 | 6 | 0.2 | 0.2 | 0.8 | 1.0 | 1.0 | 0.6 | 0.2 |
| Other formates | 2.6 | 12.1 | 0.2 | 0.1 | 1.3 | 0.5 | 3.3 | 1.1 | 0.8 |
| Miscellaneous products | 4.6 | 5.7 | 3.5 | 2.8 | 3.8 | 4.5 | 4.5 | 3.6 | 2.6 |
| Exit reactor (i.e., stream 5) liquid phase (kg/hr) | 19.442 | 21.039 | 21.680 | 22.3 | 19.590 | 13.060 | 18.720 | 28.758 | 21.370 |
| Composition (% weight) | | | | | | | | | |
| $H_2O$ | 0.08 | 0.14 | 0.02 | 0.03 | 0.03 | 0.12 | 0.09 | 0.05 | 0.03 |
| $N_2 + O_2$ | 0.36 | 0.22 | 0.19 | 0.17 | 0.31 | 0.31 | 0.28 | 0.14 | 0.19 |
| $C_3H_6$ | 9.82 | 8.47 | 12.64 | 10.98 | 13.04 | 14.89 | 13.06 | 8.95 | 13.14 |
| $CO_2$ | 0.19 | 0.19 | 0.15 | 0.12 | 0.18 | 0.25 | 0.16 | 0.13 | 0.15 |
| POX* | 2.00 | 2.42 | 1.03 | 0.84 | 1.73 | 2.30 | 1.55 | 1.31 | 1.36 |
| PGL* | 0.09 | 0.08 | — | — | 0.03 | 0.06 | 0.03 | — | 0.07 |
| solvent | 85.05 | 85.68 | 85.10 | 87.16 | 83.58 | 80.24 | 83.50 | 88.35 | 84.30 |
| HCOOH | 0.47 | 0.52 | 0.11 | 0.12 | 0.22 | 0.26 | 0.22 | 0.21 | 0.10 |
| $CH_3COOH$ | 0.30 | 0.43 | 0.10 | 0.07 | 0.11 | 0.17 | 0.11 | 0.16 | 0.08 |
| HCOOMe | 0.20 | 0.24 | 0.04 | 0.01 | 0.07 | 0.11 | 0.11 | 0.05 | 0.05 |
| Other formates | 0.18 | 0.27 | — | — | 0.04 | 0.14 | 0.03 | 0.01 | 0.02 |
| Miscellaneous products | 0.69 | 0.88 | 0.42 | 0.38 | 0.56 | 0.73 | 0.60 | 0.44 | 0.36 |
| Heavy products | 0.57 | 0.46 | 0.20 | 0.12 | 0.10 | 0.42 | 0.26 | 0.20 | 0.15 |

*Abbreviations:
POX: propylene oxide
PGL: propylene glycol
TCB: 1,2,4-trichlorobenzene

TABLE 2

| Examples | 10 | 11 | 12 | 13 | 14 | 15 |
|---|---|---|---|---|---|---|
| Feed to reactor A | | | | | | |
| solvent* | MCB | MCB | MCB | MCB | A | A |
| solvent rate (kg/hr) | 14.464 | 15.100 | 15.020 | 14.980 | 7.736 | 6.280 |
| $C_3H_6$ (kg/hr) | 4.437 | 3.879 | 6.570 | 6.600 | 3.304 | 2.439 |
| air (m³/hr) | 1.613 | 1.494 | 3.770 | 3.742 | 1.418 | 1.679 |
| Gases Leaving Condenser B | | | | | | |
| gas rate (m³/hr) | 1.773 | 1.592 | 3.845 | 3.845 | 1.457 | 1.608 |
| Composition (volume %) | | | | | | |
| $O_2$ | 0.8 | 0.9 | 0.7 | 0.8 | 1.2 | 0.5 |
| $N_2$ | 71.7 | 70.2 | 74.4 | 74.2 | 71.9 | 78.5 |
| $C_3H_6$ | 23.8 | 25.0 | 20.2 | 20.4 | 24.2 | 18.8 |
| CO | 0.9 | 1.0 | 1.0 | 0.9 | 0.9 | 1.1 |
| $CO_2$ | 2.7 | 2.9 | 3.7 | 3.7 | 1.8 | 1.1 |
| Aqueous Phase Leaving Decantation Device D (kg/hr) | 0.050 | 0.504 | 0.144 | 0.820 | 0 | 0 |
| composition (% weight) | | | | | | |
| $H_2O$ | 49.1 | 83.7 | 40.7 | 71.1 | — | — |
| PGL* | 7.1 | 3.5 | 11.8 | 7.1 | — | — |
| HCOOH | 25.3 | 8.0 | 23.3 | 12.1 | — | — |
| $CH_3COOH$ | 1.0 | 0.7 | 2.6 | 1.6 | — | — |
| HCOOMe | 7.3 | 0.5 | 8.0 | 1.8 | — | — |
| other formates | 4.0 | 0.3 | 7.0 | 1.1 | — | — |
| miscellaneous products | 6.2 | 3.3 | 8.6 | 5.2 | — | — |
| Exit reactor (i.e., stream 5) liquid phase (kg/hr) | 18.410 | 18.544 | 20.890 | 20.715 | 10.800 | 8.659 |
| composition (% weight) | | | | | | |
| $H_2O$ | 0.06 | 0.04 | 0.15 | 0.12 | 0.39 | 0.53 |
| $N_2 + O_2$ | 0.02 | 0.42 | 0.70 | 0.63 | 0.92 | 0.94 |
| $C_3H_6$ | 16.51 | 13.92 | 18.66 | 18.86 | 19.95 | 14.80 |
| $CO_2$ | 0.12 | 0.28 | 0.63 | 0.54 | 0.59 | 0.60 |
| POX* | 2.05 | 1.79 | 3.33 | 3.35 | 2.53 | 3.68 |
| PGL* | 0.07 | 0.06 | 0.08 | 0.08 | 0.07 | 0.13 |
| solvent | 78.56 | 81.43 | 71.87 | 72.30 | 71.62 | 72.52 |

TABLE 2-continued

| Examples | 10 | 11 | 12 | 13 | 14 | 15 |
| --- | --- | --- | --- | --- | --- | --- |
| H COOH | 0.64 | 0.52 | 1.31 | 1.14 | 0.98 | 1.88 |
| CH₃ COOH | 0.30 | 0.20 | 0.53 | 0.45 | 0.44 | 1.24 |
| H COO Me | 0.16 | 0.12 | 0.43 | 0.38 | 0.16 | 0.25 |
| other formates | 0.09 | 0.05 | 0.05 | 0.06 | 0.27 | 0.44 |
| miscellaneous products | 0.95 | 0.83 | 1.30 | 1.32 | 1.22 | 1.78 |
| heavy products | 0.47 | 0.34 | 0.96 | 0.77 | 0.86 | 1.21 |

*Abbreviations:
MCB: monochlorobenzene
A   : acetone
POX: propylene oxide
PGL: propylene glycol

TABLE 3

| Ex. | Solvent | Reaction Temperature (°C) | Reactor Pressure (Bars) | Residence Time (hour) | Amount of $H_2O$ added to Condensed Products (kg/m³ of $O_2$) | H COOH Removed (%) | H COO Me Produced (kg/100 kg POX) | Total of Formates (kg/100 kg POX + PGL) | Heavy Products (kg/100kg (POX+PGL) | Conversion Rate $C_3H_6$ (%) | Selectivity POX + PGL (%) | POX hydroxylated to PGL (%) |
| --- | --- | --- | --- | --- | --- | --- | --- | --- | --- | --- | --- | --- |
| 1 | TCB | 163 | 60 | 0.38 | 0 | 30.9 | 13.1 | 21.7 | 27.1 | 25.8 | 43.9 | 3.3 |
| 2 | TCB | 183 | 60 | 0.36 | 0 | 30.0 | 12.3 | 26.0 | 16.9 | 33.8 | 44.1 | 8.2 |
| 3 | TCB | 163 | 60 | 0.32 | 4.543 | 63.7 | 4.5 | 4.7 | 18.4 | 11.5 | 46.8 | 3.3 |
| 4 | TCB | 164 | 60 | 0.32 | 4.309 | 54.6 | 1.9 | 8.1 | 13.7 | 10.6 | 48.4 | 4.4 |
| 5 | TCB | 166 | 60 | 0.36 | 1.543 | 54.7 | 4.7 | 7.6 | 5.4 | 15.5 | 55.8 | 6.5 |
| 6 | TCB | 164 | 60 | 0.52 | 1.386 | 53.9 | 6.3 | 13.1 | 16.1 | 19.4 | 50.5 | 8.2 |
| 7 | TCB | 165 | 60 | 0.38 | 1.114 | 50.4 | 8.3 | 13.3 | 15.2 | 15.3 | 50.9 | 6.7 |
| 8 | TCB | 180 | 60 | 0.26 | 1.429 | 55 | 4.5 | 6.3 | 13.3 | 19.1 | 49.8 | 9.5 |
| 9 | TCB | 165 | 60 | 0.33 | 1.352 | 52.6 | 3.9 | 4.8 | 9.3 | 12.3 | 58.8 | 11.2 |
| 10 | MCB | 165 | 56 | 0.31 | 0 | 9.9 | 8.8 | 12.8 | 21.7 | 16.6 | 46.6 | 3.2 |
| 11 | MCB | 165 | 56 | 0.31 | 1.924 | 29.5 | 7.2 | 8.9 | 17.3 | 17.6 | 46.5 | 6.2 |
| 12 | MCB | 165 | 80 | 0.26 | 0 | 10.9 | 14.4 | 16.5 | 26.8 | 23.8 | 42.9 | 3.6 |
| 13 | MCB | 165 | 80 | 0.26 | 0.695 | 29.6 | 13.5 | 14.9 | 20.5 | 23.9 | 44.4 | 7.6 |
| 14 | A | 165 | 56 | 0.40 | 0 | 0 | 5.8 | 15.5 | 33.2 | 18.4 | 41.4 | 2.1 |
| 15 | A | 166 | 56 | 0.51 | 0 | 0 | 6.6 | 17.0 | 31.6 | 31.4 | 40.3 | 2.7 |

Abbreviations: TCB: 1,2,4-trichlorobenzene
MCB: monochlorobenzene
A : acetone

While the invention has been described with reference to the preferred embodiments thereof, it is to be understood that various changes, modifications and/or substitutions may be made therein without departing from the spirit and scope thereof. It is the intention, therefore, that the invention be limited only by the scope of the appended claims.

What is claimed is:

1. In a liquid phase continuous process for producing propylene oxide comprising oxidizing propylene by contacting propylene with a molecular oxygen-containing gas in a solvent comprising an organic solvent which is water-insoluble and is as immiscible with organic carboxylic acids as possible and selected from the group consisting of monochlorobenzene, dichlorobenzene, trichlorobenzene and tetrachlorobenzene and mixtures thereof at a temperature and pressure necessary for the oxidation reaction and condensing the gaseous reaction products, the improvement comprising:

adding to the condensed gaseous reaction products an amount of water necessary to dissolve substantially any undissolved organic carboxylic acids present therein thereby producing a two-phase system comprising (1) an aqueous phase containing said acids and (2) an organic phase containing said solvent and unreacted propylene;

separating said aqueous phase from said two-phase system and recycling said organic phase to said reaction;

removing a liquid containing propylene oxide from the reaction system; and recovering said propylene oxide from said liquid.

2. The process of claim 1 wherein said amount of water is from 0 to 5 kg per m³ of oxygen (N.T.P.) fed to the reaction.

3. The process of claim 2 wherein the temperature and pressure of reaction is 120°–250°C. and 30–100 Bars, respectively.

4. The process of claim 2 wherein said condensation is performed at a temperature of from about 15° to about 20°C., thereby producing a gas and a liquid phase, further comprising venting said gas phase and adding said amount of water to said liquid phase.

5. The process of claim 4 wherein water is added to said liquid phase at a temperature of less than 25°C.

6. The process of claim 5 wherein the temperature and pressure of reaction are 140°–200°C. and 40–80 Bars, respectively.

7. The process of claim 1 wherein the reaction is performed in the presence of a catalytic amount of an oxidation catalyst.

8. The process of claim 7 wherein said catalyst is selected from the group consisting of naphthenates and acetylacetonates of molybdenum, tungsten and vanadium.

* * * * *